United States Patent [19]
Liu

[11] Patent Number: 6,045,791
[45] Date of Patent: *Apr. 4, 2000

[54] RETINAL PIGMENT EPITHELIUM TRANSPLANTATION

[75] Inventor: Yao Liu, Philadelphia, Pa.

[73] Assignee: Photogenesis, Inc., Los Angeles

[*] Notice: This patent is subject to a terminal disclaimer.

[21] Appl. No.: 08/444,416

[22] Filed: May 19, 1995

Related U.S. Application Data

[63] Continuation of application No. 07/848,407, Mar. 6, 1992, abandoned.

[51] Int. Cl.⁷ ................................................. C12N 5/06
[52] U.S. Cl. .................... 424/93.7; 435/366; 435/371; 623/4
[58] Field of Search ................ 435/174, 240.2, 435/240.21, 240.23, 240.243, 325, 366, 371; 623/4, 5; 424/93.7

[56] References Cited

U.S. PATENT DOCUMENTS

| | | | |
|---|---|---|---|
| 3,934,591 | 1/1976 | Gleason | 128/305.5 |
| 4,014,342 | 3/1977 | Staub et al. | 128/305.1 |
| 4,304,866 | 12/1981 | Green et al. | 435/240 |
| 4,418,691 | 12/1983 | Yannas et al. | 128/156 |
| 4,495,288 | 1/1985 | Jarvis, Jr. et al. | 435/241 |
| 4,563,779 | 1/1986 | Kelman | 623/5 |
| 4,655,774 | 4/1987 | Choyce | 623/5 |
| 4,662,869 | 5/1987 | Wright | 604/22 |
| 4,689,399 | 8/1987 | Chu | 530/356 |
| 4,693,686 | 9/1987 | Sendax | 433/173 |
| 4,702,697 | 10/1987 | Linkow | 433/173 |
| 4,727,018 | 2/1988 | Eichner et al. | 435/1 |
| 4,868,116 | 9/1989 | Morgan et al. | 435/240.2 |
| 4,900,300 | 2/1990 | Lee | 604/22 |
| 4,927,676 | 5/1990 | Williams | 428/36 |
| 4,940,468 | 7/1990 | Petillo | 606/170 |
| 4,963,489 | 10/1990 | Naughton et al. | 435/240.1 |
| 5,000,963 | 3/1991 | Hefton | 424/574 |
| 5,273,530 | 12/1993 | Del Cerro et al. | 604/51 |
| 5,292,802 | 3/1994 | Rhee et al. | 525/54.1 |
| 5,308,889 | 5/1994 | Rhee et al. | 523/113 |
| 5,322,691 | 6/1994 | Darouger et al. | 424/427 |
| 5,323,788 | 6/1994 | Silvestrini et al. | 128/897 |
| 5,324,260 | 6/1994 | O'Neill et al. | 604/96 |
| 5,326,346 | 7/1994 | Cortes | 623/4 |
| 5,326,584 | 7/1994 | Kamel | 427/491 |
| 5,328,481 | 7/1994 | Wang | 604/51 |
| 5,342,370 | 8/1994 | Simon et al. | 606/107 |
| 5,374,515 | 12/1994 | Parenteau et al | 435/1 |
| 5,409,457 | 4/1995 | Del Cerro et al. | 604/51 |

FOREIGN PATENT DOCUMENTS

| | | |
|---|---|---|
| 0 340 698 | 11/1989 | European Pat. Off. . |
| 0 535 506 A1 | 4/1993 | European Pat. Off. . |
| 40 04 921 A1 | 8/1991 | Germany . |
| WO 91/02499 | 3/1991 | WIPO . |
| WO 92/08406 | 5/1992 | WIPO . |

OTHER PUBLICATIONS

Zucker, "Synaptic Microcircuitry of Rat Retinal Transplants Ultrastructural Observations", Suppl., Invest. Ophthalmol. Vis. Sci., 31:594, abs. # 2906–4, 1990.

Valentino, "Photoreceptor rescue in RCS rat and rd mouse by heat shock", Suppl., Invest. Ophthalmol. Vis. Sci., 31:594, abs. # 2911–9, 1990.

Valention, "Photoreceptor sheets isolated from the neonatal rat retina lack synapses and other retinal cells", Soc. Neuroscience. 18:838, abs # 352–8, Oct. 25–30, 1992. Part I.

Vinores, "Ultrastructural Localization of RPE Epitopes in In Situ and Clutrued RPE Cells and their Expression in Fibroblasts in Vitreous Culture", Soc. Neurosci. 16:405, abs. # 171.4, 1990.

Weiss, "Transplanting the Light Fantastic Cells from eye donors may someday restore vision in some blind individuals", Science News, vol. 136, No. 19, pp. 297–300, Nov. 4, 1989.

Wilcheck, "Immobilization of Enzymes and Affinity Ligands onto Agarose Via Stable and Uncharged Carbamate Linkages", Biochem. Int'l. vol. 4, No. 6, pp. 629–635, Jun. 1982.

Wise, Lactic/Glycolic Acid Polymer, Drug Carriers in Biology and Medicine (ed. Gregoriaris) 1979 Chapter 12, pp. 237–270.

Tootell, "Deoxyglucose analysis of retinotopic organization in primate striate cortex", Sci. 218:902–904, Nov. 26, 1982.

Tootell, "Two Methods for flat–mounting cortical tissue", Journal Neurosci. Methods, 15:177–190, 1985.

Townes, Anderson "Rod Photoreceptors Dissociated from the Adult Rabbit Retina", Jour. Of Neuroscience, vol. 8, No. 1, pp. 320–331, Jan., 1988.

Tuliusson, Reversed Ratio of Color Specific Cones in Rabbit Retinal Transplants, Invest. Ophthalmol. Vis. Sci. 34:1096, abs # 1936–92, Mar. 1993.

(List continued on next page.)

*Primary Examiner*—Jean C. Witz
*Attorney, Agent, or Firm*—Daniel B. Schein, Esq.

[57] ABSTRACT

An implant is provided for transplantation to the subretinal area of a host's eye comprising a laminate of a monolayer of retinal pigment epithelium (RPE) cells and a non-toxic, flexible support that, upon exposure to a set of predetermined conditions, will not impede normal eye tissue function. A method for preparing a population of RPE cells for transplantation to the subretinal area of a host eye is also provided. The method includes the steps of providing donor tissue comprising RPE cells, harvesting from that tissue RPE cells, and apposing the harvested RPE cells as a monolayer to a non-toxic, flexible support that, upon transplantation to the subretinal area and exposure to a set of predetermined conditions, will not impede normal eye tissue function of the host eye and the transplanted population. A method for transplanting the above implant is also provided, comprising providing the implant, making an incision through a host's eye, at least partially detaching the retina to permit access to the subretinal area, and positioning the implant in the accessed area.

9 Claims, 7 Drawing Sheets

OTHER PUBLICATIONS

Turner, "Newborn Rat Retinal Cells Transplanted Into a Retinal Lesion Site In Adult Host Eyes", Develop. Brain Research, 26:91–104, (1986).

Valentino, Transplanted photoreceptors form synapses in reconstructed RCS rat retina. Soc. Neurosci., 16:405, abs # 171.2, Oct. 28– Nov. 2, 1990.

Sokoloff, "the [C]Deoxyglucosel Method for the Measurement of Local Cerebral Glucose Utilization: Theory, Procedure, and Normal Values in the Conscious and Anesthetized Albino Rat", Jour. of Neurochem., 28:897–916, 1977.

Solomons, Special Topic M Photochemistry of Vision Organic Chemistry. 5th Ed., Univ. of Fl, Pub. Wiley & Sons, pp. 1168–1171, 1991.

Tien, In Search of A Receptor for Outer Segments in Rat Retinal Pigmented Epithelium, Soc. Neurosci. 16:405, abs # 171.3, 1990.

Tootell, "Deoxyglucose mapping of color and spatial frequency organization in monkey and Cat Cortex", Recent Advances in Vision. Optical Society of America Techn. Digest. SA14, 1980.

Tootell, "Color–Dependent Deoxyglucose Patterns Within Macaque Cortex". Arvo Abstracts 226, Suppl., Invest. Ophthalmol. Vis. Sci. pp. 226, abs. # 12, Apr. 1980.

Tootell, "2DG study of retinotopic organization in macaque striate cortex", Suppl., Invest. Ophthalmol. Visual Sci. 22:12, # 3, abs. # 14, Mar. 1982.

Silverman, "Photoreceptor transplantation: Anatomic, electrophysiologic and behavioral evidence for the functional reconstruction of retinas lacking photoreceptors". Soc. Neurosci. 17:12, abs. # 9.4, Nov. 10–15, 1991. Pt. I.

Silverman, "Photoreceptor transplantation: Anatomic, electrophysiologic and behavioral evidence for the functional reconstrution of retinas lacking photorecptors", Experimental Neurology 115:87–94, 1992.

Silverman, "Rescue of host cones by transplanted donor photoreceptors in the rd mouse", Invest. Ophthalmol. Vis. Sci. 34:1096, # 4, abs. # 1937–93, Mar. 15, 1993.

Silverman, Transplantation of Retinal Photoreceptors to Light–Damaged Retina, 288 Arvo Abstracts, abs. # 11, Suppl. Invest Ophthalmol Vis. Sc., vol. 28.

Silverman, "A comparison of Ocular Dominance Patterns in Cat and Monkey", Suppl. Invest. Ophthalmol. Visual Sci. 22:12, # 3, abs. # 13, Mar. 1982.

Simmons, "Physiological Responses in Retinal Transplants and Host Tecta Evoked by Electrical or Photic Stimulation of Transplanted Embryonic Retinae", Soc. Neurosci. Abstr. 10:668, abs # 196.5.

Silverman, "Transplantation of Human and Non–Human Primate Photoreceptors to Damaged Primate Retina", Invest. Ophthalmol. Visual Sci., 31:594, abs # 2909–7, 1990.

Silverman, "Photoreceptor rescue in the RCS rat without pigment epithelium transplantation", Curr. Eye Res. 9:183–192, # 2, 1990.

Silverman, "Photoreceptor transplantation to dystrophic retina. Retinal Degeneration", (ed. Anderson R.E., LaVail, MM, and Hollyfield J.G.). CRC Press, Inc., Boca Raton, Florida, pp. 321–335, Chapter 29, 1991.

Silverman, "Restoration of the pupillary reflex by photoreceptor transplantation", Suppl., Invest. Ophthalmol. Vis. Sci. 32:983, abs # 1548, 1991.

Ferguson, "Effect of Genetic Disparity on Photoreceptor Transplant Survival", Suppl., Invest. Ophthalmol. Vis. Sci. 32:983, abs # 1549.

Silverman, Transplantation of retinal photoreceptors to light damaged retina: Survival and integration of receptors from a range of postnatal ages, Soc. Neurosci. Abstr. 17:1301, abs. # 360.17, 1987.

Silverman, "Photoreceptor transplantation in inherited and environmentally induced retinal degeneration: Anatomy, Immunohistochemistry and Function. Inherited and Environmentally Induced Retinal Degeneration", (ed., MM LaVail, RE Anderson, and JG Hollyfield) Alan r. Liss publisher, pp. 687–704, 1989.

Silverman, "Photoreceptor rescue in the RCS rat without pigment epithelium transplantation", Soc. Neurosci., 15:115, abs # 51.1, Oct. 29– Nov. 3, 1989. Pt. I.

Silverman, "Transplantation of Photoreceptors to Light Damaged Retina", Invest. Ophthalmol. Vis. Sci., vol. 30, No. 8, 1684–1690, Aug. 1989.

Silverman, "Deoxyglucose mapping of Orientation and spatial frequency in cat visual cortex", Suppl., Invest. Ophthalmol. Visual Sci. 18:255, abs # 10, 1980.

Silverman, "Deoxyglucose mapping of orientation in cat visual cortex", Recent Advances in Vision. Optical Society of America Technical Digest. SA13, 1980.

Silverman, "The retinotopic organization of cat striate cortex", Suppl. Invest Ophthalmol. Visual Sci. 22:105, abs. # 1, 1982.

Silverman, Transplantation of retinal photoreceptors to light damaged retina, Suppl., Invest. Ophthalmol. Vis. Sci. 28:288, abs # 11, 1987.

Sarthy, Isolated Cells from a Mammalian Retina, Brain Research, 176:208–212, 1979.

Schuschereba, "Retinal cell and photoreceptor transplantation between adult New Zealand Red Rabbit Retinas", Experimental Neurology. 115:95–99, 1992.

Seaton, "Inhibition of Neovascularization by the Transplantation of Healthy Retinal Pigment Epithelial Cells into the RCS Rat", Suppl., Invest. Ophthalmol. Vis. Sci. 32:983, abs # 1547, 1991.

Sheedlo, "Photoreceptor Cell Rescue by RPE–Cell Grafts in RCS Rats at Early and Late Stages of Retinal Dystrophy", Suppl., Invest. Ophthalmol. Visual Sci., 30:208, abs # 10, 1989.

Sheedlo, Functional and Structural Characteristics of Photoreceptor Cells Rescued in RPE–cell Grafted Retinas of RCS Dystrophic Rats, 48:841–854, 1989.

Shiosaka, "A simple method for the separation of retinal sublayers from the entire retina with special reference to application for cell culture", Jour. Neurosci. Methods, 10:229–235, 1984.

Powell, "Controlled release of nerve growth factor from a polymeric implant", Brain Res., 515:309–311, 1990.

Pu, "Biochemical Interruption of Membrane Phospholipid Renewal in retinal Photoreceptor Cells", Jour. of Neurosci., vol. 4, No. 6, pp. 1559–1576, Jun. 1984.

Radel, "Quantification of Light–Activated Pupilloconstriction in Rats Mediated by Intracranially Transplanted Retinae", Suppl. Invest. Ophthalmol. Vis. Sci. 32:983, abs # 1550, 1991.

Radtke, "Pharmacological Therapy for Proliferative Vitreoretinopathy", vol. 224 Graefe's Archive Ophthalmol. pp. 230–233, 1986.

Raymond, "Progenitor Cells in Outer Nuclear Layer of Goldfish Retina That Normally Produce Only Rods Produce other Neurons during Retinal Degeneration", Suppl., Invest. Ophthalmol. Vis. Sci. 28:288, abs # 13, 1987.

Royo, "Retinal Transplantation from Fetal to Maternal Mammalian Eye", Growth, 23:313–336, 1959.

Nasir, "Choriocapillaris Atrophy as a Complication of Surgical Excision of Choroidal Neovascular Membranes", Invest. Ophthalmol. Vis. Sci. 34:834, # 4, abs. # 653, Mar. 15, 1993.

Newsome, "Transplantation of Human Retinal Pigment Epithelium Into Primate Model of Macular Degeneration", Retina Society Meeting, Toronto, Canada, Sep. 1991.

O'Steen, Retinal and Optic Nerve Serotonin and Retinal Degeneration as Influenced by Photoperiod, Exp. Neurology, 27:194–205, 1970.

Petry, "Immunocytochemical Identification of Photoreceptor Populations in the Retinas of Normal and Red–Light–Reared Tree Shrews", Soc. Neuroscience, 18:838, abs # 352.9, Oct. 25–30, 1992.

Pfeffer, Improved Methodology for Cell Culture of Human and Monkey Retinal Pigment Epithelium, Chapter 10, Progress in retinal research, vol. 10, pp. 251–291, 1991.

Politi, Generation of Enriched Populations of Cultured Photoreceptor Cells, Invest. Ophthalmol. Vis. Sci., vol. 27, No. 5, pp. 656–665, May, 1986.

McCulley, "A Gelatin Membrane Substrate for the Transplantation of Tissue Cultured Cells, Transplantation", vol. 29, No. 6, pp. 498–499, Jun. 1980.

Mollenhauer, "Plastic Embedding Mixtures for use in Electron Microscopy", Stain Tech., 39:111–114.

Moritera, Transplants of monolayer retinal pigment epithelium grown on biodegradable membrane in rabbits. Invest. Ophthalmol. Vis. 34: # 4, abs. 1919–75, Mar. 15, 1993.

Muller, "Morphology and synaptic inputs to lucifer yellow injected bipolar cells in rat retinal slices", Soc. Neurosci., 17:1013, abs. # 403.4, Nov. 10–15, 1991.

Muller, "Rod and cone inputs to bipolar cells in the rat retina", Inves. Ophthalmol. Vis. Sci. 34:984, # 4, abs. # 1387, Mar. 15, 1993.

Mueller, "Autotransplantation of Retinal Pigment Epithelium in Intravitreal Diffusion Chamber", vol. 80, No. 3, Part II Retinal Pigment Epithelium, p. 530–537, 1993.

Lund, "Axonal Outgrowth from Transplanted Retinae is Stimulated by Appropriated Target Regions", Suppl., Invest. Opthalmol. Visc., 28:288, abs. # 12 (1987).

MacLeish, "Growth and Synapse Formation Among Major Classes of Adult Salamander Retinal Neurons in Vitro", Neuron, Vo. 1, pp. 751–760, Oct. 1988.

Mayerson, "An Improved Method for Isolation and Culture of Rat Retinal Pigment Epithelial Cells", Invest. Ophthalmol. & Vis. Sci., 26:1599–1609, Nov. 1985.

McConnell, "Regeneration of ganglion cell axons in the adult mouse retina", Brain Research, 241:362–365 (1982).

Maurice, "Keratoplasty with Cultured Endothelium on Thin Membranes", Arvo Abstracts, Supp. Inv. Ophthalmol. and Vis. Sci., pp. 10, abs # 9, Apr. 1979.

McCulley, "Corneal Endothelial Transplantation", Ophthalmol., vol. 87, # 3, pp. 194–201, Mar. 1980.

Li, "Optimal Coditions for Long–term Photoreceptor Cell Rescue in RCS Rats: The Necessity for Healthy RPE Transplants", Exp. Eye Res. 52:669–679, (1991).

Liu, "Photoreceptor inner and outer segments in transplanted retina", Soc. Neurosci., 16:405, abs. # 171.1, 1990.

Liu, "Transplantation of confluent sheets of adult human RPE", Invest. Ophthalmol. Vis. Sci. 33:1128, # 4, abs. # 2180, Mar. 15, 1992.

Liu, "Transplantation of confluent sheets of adult human and rat RPE on a thin substrate", Suppl., Invest. Ophthalmol. Vis. 34:1112, abs. # 2018–50, 1993.

Lopez, "Transplanted retinal Pigment Epithelium Modifies the Retinal Degeneration in the RCS Rat", Invest. Ophthalmol. & Vis. Sci., 30:586–589, # 3, Mar. 1989.

Lopez, "Transplantation of Human RPE Cells into the Monkey", Suppl. Invest. Ophthalmol. Vis. Sci., 31:594, abs # 2910–8, 1990.

LaVail, "Histotypic Organization of the Rat Retina in Vitro", Z. Zellforsch, Springer Verlag, 114:557–579, 1971.

LaVail, "Multiple Growth factors, Cytokines, and Neurotrophins Rescue Photoreceptors from the Damaging Effects of Constant Light", Neurobiology, vol. 89, pp. 11249–11253, Dec. 1992.

LaVail, "RPE Cell Transplantation in RCS Rats: Normal Metabolism in Rescued Photoreceptors", Suppl., Invest. Ophthalmol. Vis. Sci. 33:1127, # 4, abs. # 2176, Mar. 15, 1992.

Lee, "Transplantation of Cultured Retinal Pigment Epithelium to Rabbit Retina Injured by Sodium Iodate", Suppl., Invest. Ophthalmol. Vis. Sci. 33:1127, # 4, abs # 2175, Mar. 15, 1992.

Li, "Transplantation of Retinal Pigment Epithelial Cells to Immature and Adult Rat Hosts: Short– and Long–term Survival Characteristics", Exp. Eye Res. 47:771–785 (1988).

Li, "Inherited Retinal dystrophy in the RCS Rat: Prevention of Photoreceptor Degeneration by Pigment Epithelial Cell Transplantation", Exp. Eye Res. 47:911–917, (1988).

Kitchell, "Poly(lactic/glycolic acid) biodegradable Drug––Polymer Matrix Systems", Methods in Enzymology, 112:436–448, Chapter 32, (1985).

Klassen, "Retinal transplants can drive a pupillary reflex in host rat brains", Proc. Natl. Acad. Sci. U.S.A., vol. 84, pp. 6958–6960, Oct. 1987.

Klassen, "Anatomical and Behavioral Correlates of a Xenograft–Mediated Pupillary Reflex", Experimental Neurology 102, 102–108, (1988).

Kordower, "Fetal Monkey Retina Transplanted into Adult Rat Eyes", Supp. Invest. Ophthalmol. Visual Sci., 30:208, abs. # 7, (1989).

Kruszewska, "Ultrastructure and Transduction in the Caudal Photoreceptor of Crayfish", Soc. Neurosci. 16:405, abs. # 171.5, 1990.

Lane, Transplantation of Retinal Pigment Epithelium Using a Pars Plana Approach, Eye, 3:27–32, 1989.

Hughes, "Differential survival of sensory elements in intracranial otic transplants", Soc. Neurosci., 17:1138, abs. # 452.12, Nov. 10–15, 1991.

Hughes, "Quantification of synapses in light–damaged retina reconstructed by transplantation of photoreceptors", Invest. Ophthalmol. Vis. Sci., # 4, 33:1058, abs. 1832–3, Mar. 15, 1992.

Hughes, "Explorations of optic transplantation", Experimental Neurology, 115:37–43, 1992.

Jacobs, "An Ultraviolet–Sensitive Cone in the Gerbil Retina", Soc. Neuroscience, 18:838, abs # 352.10, Oct. 25–30, 1992.

Jiang, "Intraocular Retinal Transplantation in Retinal Degeneration (rd/rd) Murine Strains", Suppl., Invest. Ophthalmol. Visual Sci., 30:208, abs. # 5, (1989).

Kaplan, "Retinal pigment epithelium regeneration in the non–human primate", Suppl., Invest. Ophthalmol. Vis. Sci. # 4, abs. # 2173, Mar. 15, 1992.

Gouras, "Anatomy and Physiology of Photoreceptor Transplants in Degenerate C3H Mouse Retina", Invest. Ophthalmol. Vis. Sci. 34:1096, # 4, abs. # 1938–94, Mar. 15, 1993.

Hicks, "Different Rhodopsin Monoclonal Antibodies Reveal Different Binding patterns on Developing and Adult Rat Retina", Jour. of Histochemistry & Cytochemistry, vol. 35, No. 11, pp. 1317–1328, (1987).

Honig, "Fluorescent Carbocyanine Dyes Allow Living Neurons of Identified Origin to be Studied in Long–term Cultures", Jour. of Cell Biology, 103:171–187, Jul. 1986.

Hughes, "Whole Cell Recordings of Isolated Retinal Pigment Epithelial Cells of the Frog", Soc. Neurosci. Abstr. 17:1301, abs. # 360.18, 1987.

Hughes, "Transplantation of Retinal Photoreceptors to Dystrophic Retina", Society Sci. Abstr. 1277, abs. # 511–16, Nov. 1988.

Hughes, "Transplanted Photoreceptors Form Synapses in Light–Damaged Retina", Suppl. Invest. Ophthalmol. Vis. Sci., 31:594, abs. # 2908–6, 1990.

Fischer, "Photoreceptor Topography in the Retinae of Anubis Baboons", Soc. Neuroscience 18:838, abs. # 352.7, Oct. 25–30, 1992.

Garcia, "Comparison of Allogeneic and Syngeneic RPE Transplants in Renal Subcapsular Space", Invest Ophthalmol. Vis. 34:1112, abs. # 2017–49, 1993.

Gao, "Low immunogenicity of neonatal murine photoreceptor cells for cytotoxic lymphocytes in mice", Invest. Ophthalmol. Vis. Sci. 33:1285, # 4, abs # 2963, Mar. 15, 1992.

Gelanze, "Survival of Photoreceptors Transplanted to the Subretinal Space of Adult RCS Rats", Suppl. Invest. Ophthalmol. Visual Sci., 30:208, abs. # 8, (1989).

Gouras, "Reconstruction of Degenerate rd Mouse Retina by Transplantation of Transgenic Photoreceptors", Invest. Ophthal. & Vis. Sci., vol. 33/9, pp. 2579–2586, Aug. 1992.

Gouras, "Transplanted Photoreceptors Form Mature Outer Segments in Degenerate rd Mouse Retina", Invest. Ophthalmol. Vis. Sci. 33:1128, # 4, abs # 2180, Mar. 15, 1992.

Du, "Neonatal Mouse Photoreceptor Transplants Replace the Photoreceptor Layer of the Host", Invest Ophthalmol. Vis. Sci. 34:1096, # 4, abs. # 1934–90, Mar. 15, 1992.

Edwards, "Light–Regulated Protein Phosphatase Activity in Limulus Ventral Photoreceptors", Soc. Neurosci. 16:405, abs. # 171.6, 1990.

Faktorovich, "Photoreceptor Degeneration in Inherited Retinal Dystrophy Delayed by Basic Fibrolast Growth Factor", Nature, 347:83–86, Sep. 6, 1990.

Faktorovich, "Basic Fibroblast Growth Factor and Local Injury Protect Photoreceptors from Light Damage in the Rat", vol. 12(9) Journal of Neuroscience pp. 3554–3567, Sep. 1992.

Fang, "Development of a surgical procedure and instrument for transplantation of extended gelatin sheets to the subretinal space", Invest. Ophthalmol. Vis. Sci. 34:1096, # 4, abs. # 1918–1974, Mar. 15, 1993.

Ferguson, "Effect of genetic disparity on photoreceptor transplant survival", Invest. Ophthalmol. Vis. Sci. 32:983, # 4, abs # 1549, Mar. 15, 1991.

del Cerro, "Retinal Transplants", Progress in Retinal Research vol. 9, chapter 6, pp. 229–269, 1990. ed. N.N. Osborne et al.

del Cerro, "Selective Transplantation of Enriched Cell Populations Derived from Immature Rat Retina", Supp. Invest. Ophthalmol. Visual Sci., 30:208, abs. #6 , 1989.

Del Priore, "Transplantation of Retinal Pigment Epithelium (RPE) Onto Bruch's Memebrane in Organ Culture", Suppl., Invest. Ophthalmol. Vis. Sci. 33:1127, # 4, abs. # 2174, Mar. 15, 1992.

Del Priore, "Differential ability of aged versus young human Bruch's Membrane to support repopulation by health RPE", Invest. Ophthalmol. Vis. Sci. 34:834, # 4, abs # 652, Mar. 15, 1993.

Du, "Long Term Survival of Infant Versus Adult Photoreceptor Transplants Labeled by Tritiated Thymidine", Suppl. Invest. Ophthalmol. Vis. Sci. 32:983, abs # 1546, 1991.

ARVO "Abstract Packet for Annual Meeting" Sarasota, Florida (May 2–May 7, 1993).

Cameron; "The Cone Photoreceptor Mosaic of the Green Sunfish", Soc. Neuroscience, 18:838, abs. # 352.6, Oct. 25–30, 1992.

Cuatrecasas; "Selective Enzyme Purification by Affinity Chromatography", Biochemistry Cuatrecasas et al., 61:636–643, Aug. 9, 1968.

Custis; "Clinical Angiographic and Histopathologic Correlations in Surgically removed Subfoveal Choroidal Neovascularization", Invest. Ophthalmol. Vis. Sci., 34:834, # 4, abs # 651, Mar. 15, 1993.

del Cerro; "Intraocular Retinal Transplants", Invest. Ophthalmol, Vis. Sci., vol. 26, pp. 1182–1185, Aug. 1985.

del Cerro; "Intraretinal transplantation of fluorescently labeled retinal cell suspensions", Neurosci. Lt., 92 pp. 21–26, (1988).

Arvo; "Arvo Conference Brochure for Annual Meeting", Sarasota, Florida (May 2–May 7, 1993).

Axén; "Chemical Coupling of Peptides and Proteins to Polysaccharides by Means of Cyanogen Halides", nature, 214:1302–1304, Jun. 24, 1967.

"Biodegradable Polymers", Polysciences, Inc., Data Sheet #365, Jan. 1990.

Bhatt; "Transplantation of Human Retinal Pigment Epithelial Cells Into Rabbits", Invest. Ophthalmol. Vis., vol. 4, # 4, abs. # 1920–76, Mar. 15, 1993.

Bignami; "The Radial Glial of Muller in the Rat Retina and Their Response to Injury. An Immunofluorescence Study with Antibodies to the Glial Fibrillary Acidic (GFA) Protein", Exp. Eye Res., 28:63–69, (1979).

Bjorklund; "Neural Grafting in the Mammalian CNS", Elsevier Science Publishing B.V., Netherlands, Ch. 38, pp. 431–436, 1985.

Adolph; "Function and Structure in Isolated Subretinal Transplants", Invest. Ophthalmol. Vis. Sci. 34:1096, # 4, abs. # 1933–89, Mar. 15, 1993.

Anderson; "Retinal Detachment in the Cat; The Pigment Epithelial–Photoreceptor Interface", Invest. Ophthalmol. Vis. Schi., vol. 24, pp. 906–926, Jul. 1983.

Aramant; "Xenografting Human Fetal Retina to Adult Rat Retina", Suppl. Invest. Ophthalmol. Vis. Sci., 31:594, abs. # 2907–5, 1990.

Aramant; "The Fate of Retinal Ganglion Cells, Retrogradely Labeled with Fluorogold and Transplanted to Rate Retina", Suppl. Invest. Ophthalmol. Vis. Sci., 32:983, abs. # 1545, 1991.

Aramant; "Tracing of connections Between Retinal Transplants and Host Retina with . . . ", Invest. Ophthalmol. Vis. Sci., 34:1096, # 4, abs. # 1935–91, Mar. 15, 1993.

RETINAL PIGMENT EPITHELIUM TRANSPLANTATION

This application is a continuation of application Ser. No. 07/848,407, filed Mar. 6, 1992, now abandoned.

BACKGROUND OF THE INVENTION

The present invention relates in general to cell and tissue transplantation techniques. More particularly, the present invention is directed to techniques for transplanting populations of retinal pigment epithelium (RPE) cells as a monolayer to the subretinal region of the eye, and to methods for preparing implants comprising monolayers of RPE cells for transplantation.

The retina is the sensory epithelial surface that lines the posterior aspect of the eye, receives the image formed by the lens, transduces this image into neural impulses and conveys this information to the brain by the optic nerve. The retina comprises a number of layers, namely, the ganglion cell layer, inner plexiform layer, inner nuclear layer, outer plexiform layer, outer nuclear layer, photoreceptor inner segments and outer segments. The outer nuclear layer comprises the cell bodies of the photoreceptor cells with the inner and outer segments being extensions of the cell bodies. The choroid is a vascular membrane containing large branched pigment cells that lies between the retina and the sclerotic coat of the vertebrate eye. Atop the choroid is a membrane 1–5 microns in thickness essentially composed of collagen, known as Bruch's membrane.

Immediately between Bruch's membrane and the retina is the retinal pigment epithelium which forms an intimate structural and functional relationship with the photoreceptor cells. Among the functions performed by RPE cells is the phagocytosis of outer segment debris produced by the photoreceptors. It is believed that failure of the RPE cells to properly perform their functions such as digestion of outer segment debris leads to the eventual degeneration and loss of photoreceptor cells.

In the leading causes of visual impairment in western industrialized countries, such as age-related macular degeneration (AMD), both photoreceptors and the underlying RPE are compromised, or have degenerated. A further aspect of AMD is the frequent appearance of subretinal neovascular membranes which grow through the Bruch's membrane and the RPE and tend to hemorrhage and leak fluids into the subretinal space.

In an effort to recover what was previously thought to be an irreparably injured retina, researchers have suggested various forms of grafts and transplantation techniques, none of which constitute an effective manner for reconstructing a dystrophic retina. The transplantation of retinal cells to the eye can be traced to a report by Royo et al., *Growth* 23: 313–336 (1959) in which embryonic retina was transplanted to the anterior chamber of the maternal eye. A variety of cells were reported to survive, including photoreceptors. Subsequently del Cerro was able to repeat and extend these experiments (del Cerro et al., *Invest. Ophthalmol. Vis. Sci.* 26: 1182–1185, 1985). Soon afterward Turner, et al. *Dev. Brain Res.* 26:91–104 (1986) showed that neonatal retinal tissue could be transplanted into retinal wounds.

Li and Turner, *Exp. Eye Res.* 47:911 (1988) have proposed the transplantation of retinal pigment epithelium (RPE) into the subretinal space as a therapeutic approach in the RCS dystrophic rat to replace defective mutant RPE cells with their healthy wild-type counterparts. According to their approach, RPE were isolated from 6- to 8-day old black eyed rats and grafted into the subretinal space by using a lesion paradigm which penetrates through the sclera and choroid. A 1 μl bolus injection of RPE (40,000–60,000 cells) was made at the incision site into the subretinal space by means of a 10 μl syringe to which was attached a 30 gauge needle. However, while this technique is marginally appropriate for immature RPE cells, with mature cells it leads to activation and transformation of these cells which damages eye and retinal tissue.

Lopez et al., *Invest. Ophthalmol. Vis. Sci.* 30: 586–589, 1989, also reported a procedure for the transplantation of dissociated RPE cells. In this procedure, RPE cells were obtained from normal, congenic, pigmented rat eyes by trypsin digestion. These freshly harvested, dissociated RPE cells were injected into the subretinal area of the eyes of dystrophic RCS rats via an incision through the sclera, choroid and neural retina. Comparable to the Li and Turner approach discussed above, this procedure destroys the organized native structure of the transplanted RPE cells, which take the form of a confluent monolayer in a healthy eye. Moreover, the procedure is of questionable value for the transplantation of mature RPE cells. When mature RPE cells are transplanted in dissociated form, experimental results indicate that they are likely to become activated, migrate into the subretinal space, and as noted by Lane, C., et al., *Eye* (1989) 3, 27–32, invade the retina and vitreous. This activation of the transplanted, mature RPE cells can result in such pathologies as retinal pucker, massive subretinal fibrosis, retinal rosette formation, retinal detachment, and proliferative vitreoretinopathy.

The difficulties discussed above associated with the transplantation of mature RPE cells is problematic for human transplantation since available supplies of immature human RPE donor tissue are extremely limited. Moreover, the inability to use mature cells effectively prevents transplantation using autologous RPE tissue, which otherwise would be desirable to avoid the complications involving potential immunological responses faced by non-autologous transplants. Since the victims of AMD are predominantly older adults, in most cases utilizing autologous tissues for transplants would necessarily entail the use of mature human RPE cells.

It is believed by the present inventor that it is necessary to maintain adult human RPE cells substantially as a monolayer to achieve their successful transplantation and to avoid the problems associated with activation of RPE cells. Although not wishing to be limited to a particular theory, it is thought that the cell-to-cell contact inhibition provided by an intact monolayer, supplemented by adherence to a substrate, mitigates against RPE cell activation. Moreover, a monolayer structure for the RPE provides a proper foundation for the maintenance of the photoreceptor cells in an organized outer nuclear layer structure and for proper growth and arrangement of inner and outer segments, believed by this inventor to be advantagous to restore a reasonable degree of vision. The requirement that the photoreceptors be maintained in an organized structure is based on the well known optical characteristics of photoreceptors (outer segments act as light guides) and clinical evidence showing that folds or similar, even minor, disruptions in the retinal geometry can severely degrade visual acuity.

Additionally, in cases of AMD where subretinal neovascular membranes have appeared, prior to RPE transplantation, such membranes will need to be removed to prevent subretinal edemas and hemorrhaging of these membranes. In practice, removal of the neovascular membrane results in removal of the native RPE and Bruch's membrane as well.

A critical impediment to the transplantation of RPE cells as a monolayer is the fragility of the intercellular structure of RPE relative to the rigors of manipulation during transplantation to the subretinal area. Moreover, providing satisfactory support to the RPE cells during this process is complicated by the fact that the support must either be removed subsequent to transplantation, to avoid compromising metabolic exchange between the choroid and the overlying retina, or be compatible with such ongoing physiological activity. Thus, a method is needed wherein an implant comprising a monolayer of RPE cells is prepared and transplanted in which the component supporting the monolayer of RPE cells, upon transplantation to the subretinal area and exposure to a set of predetermined conditions, does not impede normal eye tissue function. Further, a Bruch's-like membrane for attachment of the transplanted RPE cells will be needed in those cases where neovascularization has occurred and the native Bruch's membrane is removed.

SUMMARY OF THE INVENTION

Among the objects of the present invention, therefore, may be noted the provision of a method for preparation of a population of RPE cells as a monolayer for use in the reconstruction of a dystrophic RPE; the provision of such a method which allows for use of mature, and in particular, autologous, mature RPE cells as donor tissue in the reconstruction of a dystrophic RPE; the provision of an implant for use in the reconstruction of a dystrophic retina; the provision of such an implant which does not interfere with normal eye tissue function after transplantation and maintains photoreceptors and their inner and outer segments by allowing for maintenance of the native organization of the photoreceptor; the provision of such an implant which provides a membrane for attachment of the population of RPE cells especially when the native Bruch's membrane has been removed; and the provision of a method for transplantation of such implants to the subretinal area of an eye.

Briefly, therefore, the present invention is directed to a method for the preparation of a population of RPE cells for transplantation to the subretinal area of a host eye. The method comprises providing donor tissue comprising RPE cells, harvesting from that tissue RPE cells, and apposing the harvested RPE cells as a monolayer to a non-toxic, flexible support that, upon transplantation to the subretinal area and exposure to a set of predetermined conditions, will not impede normal eye tissue function of the host eye and the transplanted population.

The present invention is further directed to an implant for transplantation to the subretinal area of a host eye. The implant comprises a laminate of a monolayer of retinal pigment epithelium cells and a non-toxic, flexible support that, upon transplantation to the subretinal area and exposure to a set of predetermined conditions, will not impede normal eye tissue function.

The present invention is also directed to a method for transplanting to the subretinal area of a host's eye an implant comprising a monolayer of RPE cells. The method comprises providing an implant comprising a laminate of a monolayer of retinal pigment epithelium cells and a non-toxic, flexible support that, upon transplantation to the subretinal area and exposure to a set of predetermined conditions, will not impede normal eye tissue function, making an incision through the host's eye, at least partially detaching the retina to permit access to the subretinal area, and positioning the implant in the accessed subretinal area.

DETAILED DESCRIPTION

As used herein, the term "donor" shall mean the same or different organism relative to the host and the term "donor tissue" shall mean tissue harvested from or cultured from tissue harvested from the same or different organism relative to the host. Autologous tissue shall mean tissue harvested from or cultured from tissue harvested from the host organism. Mature RPE cells shall mean differentiated RPE cells derived from an organism that is not a fetus.

It is believed that in age-related macular degeneration (AMD), compromise or degeneration of the RPE cells which underlie and form a close structural and metabolic support for the photoreceptors, leads to the loss or destruction of viable photoreceptors. It has been discovered, however, that transplantation of a population of RPE cells as a monolayer, i.e., in essentially a two-dimensional array of cell bodies capable of engaging in cell-to-cell contact inhibition, allows the RPE cells to maintain largely normal characteristics of native, healthy retinal pigment epithelia, capable of providing structural and functional support to photoreceptor cells. Moreover, as illustrated in Example 2 below, it is believed that it is essential to transplant mature RPE cells as a monolayer in order to prevent activation of such cells. Activation leads RPE cells to transdifferentiate into wandering macrophages, fibroblast-like cells and other cell types, which cause a number of dystrophic effects in the eye and retina.

Figure 1:
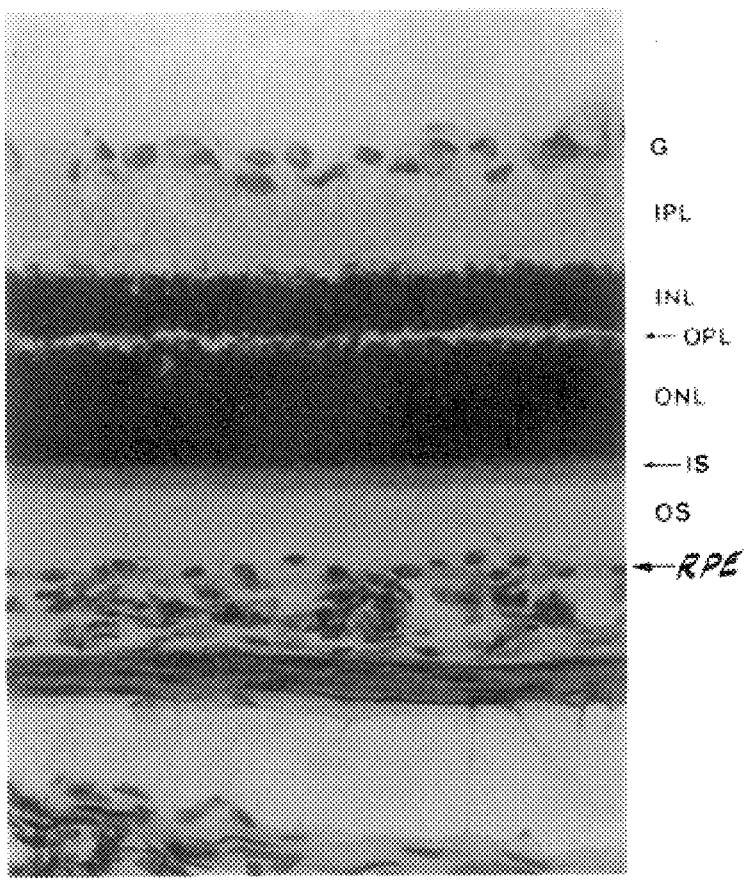
FIG. 1 is a photograph (200×) of a cryostat section of a normal rat retina and sub-retinal area.

FIG. 1 is a photograph of a cryostat section of a normal rat retina and subretinal area. In FIG. 1 as well as subsequent figures, the retina or layers thereof, e.g., the ganglion cell layer ("G"), inner plexiform layer ("IPL"), inner nuclear layer ("INL"), outer plexiform layer ("OPL"), outer nuclear layer ("ONL"), inner segments ("IS"), outer segments ("OS"), and retinal pigment epithelium ("RPE"), are shown, respectively, from top to bottom.

Referring now to FIG. 2, implants comprising a monolayer of RPE cells are prepared, in general, by harvesting RPE cells from donor tissue and apposing the harvested RPE cells as an intact monolayer to a non-toxic, flexible composition, or by seeding such a composition with a monolayer of dissociated RPE cells and allowing them to grow into a confluent layer. The flexible composition serves as a stabilizing support for the RPE cells during transplantation.

The implant constitutes a laminate of a monolayer of RPE cells and a support composition approximately 100 to 500 microns thick, and preferably 150–250 microns thick. The surface of the implant has a surface area greater than about 1 square millimeter, preferably greater than 2 square millimeters, and most preferably greater than 4 square millimeters, or as large as may be practically handled. Thus constructed, the implant may subtend a considerable extent of the sub-retinal surface.

In selecting donor tissue for the harvesting of RPE cells, it is noted that previously, transplantation of RPE cells was effectively limited to immature cells. Mature RPE cells transplanted according to prior art methods have been shown to undergo activation resulting in retinal pucker, sub-retinal fibrosis and proliferative vitreoretinopathy. However, by utilizing the procedures for implanting a monolayer of RPE cells according to this invention, transplanted mature RPE cells have successfully maintained essentially normal structure and function. Thus, the subject invention makes mature RPE cells available for transplantation, significantly increasing the supply of usable donor tissue beyond the narrowly limited supply of immature human donor tissue.

It is also noted that the RPE forms part of the blood-retinal barrier and is thus exposed to lymphocytic attack. Accordingly, use of autologous RPE cells, now possible even for mature RPE cells, is preferable, since it will avoid immunological complications in clinical applications. If non-autologous tissue is utilized, tissue typing and/or use of an immunosuppression regimen will generally be necessary to avoid rejection upon transplantation.

Donor tissue may be provided, for non-autologous, human RPE tissue, from eye banks, which make the RPE tissue available in connection with conducting corneal transplants. Harvesting donated tissue comprising non-autologous RPE cells can be accomplished by any suitable method. In general, harvesting of RPE cells may be carried out as set forth in Pfeffer, B. A., Chapter 10, "Improved Methodology for Cell Culture of Human and Monkey Retinal Pigment Epithelium", *Progress in Retinal Research,* Vol. 10 (1991); Ed. by Osborn, N. and Chader, J., or Mayerson, P. L., et al., "An Improved Method for Isolation and Culture of Rat Retinal Pigment Epithelial Cells", *Investigative Ophthalmology & Visual Science,* Nov., 1985, 26: 1599–1609, which are incorporated herein by reference. Specifically, to harvest non-autologous RPE cells, a donor eye is pinned by the optic nerve stump into an eye cage and placed in an eye jar immediately after corneal removal. The jar is then flooded to capacity with cold Delbecco's modified essential medium (DMEM) supplemented with 5% fetal bovine serum. After loose connective tissue and muscle have been carefully trimmed from the eye, it is placed upright on a sterile plate and the anterior segment with the adherent vitreous is lifted out of the eye cup. The neural retina is separated at the optic disc and removed. The shell is then washed with Hanks' balanced salt solution, Ca++ and Mg++ free, and treated with 0.25% trypsin for 30 min. at 37° C. The trypsin solution is aspirated from the shell and DMEM (GIBCO) is added. The RPE cells are released from Bruch's membrane by gently pipetting the culture medium in the shell.

For implants containing autologous tissue, RPE cells may be harvested by performing a biopsy following the procedures disclosed by Lane, C., et al. in *Eye* (1989) 3, 27–32.

The implant also comprises a support for the RPE cells so that the monolayer of RPE cells is less likely to be damaged and is more easily manipulated during the transplantation process. The support consists of a substrate, an overlayer or both, comprising a sheet or sheets of a non-toxic, flexible composition selected to provide mechanical strength and stability to the easily damaged monolayer of RPE cells. Because the support composition will be inserted into the eye as a laminate with the monolayer of RPE cells, the support is also comprised so that, upon transplantation to the subretinal area and exposure to a set of predetermined conditions, described herein, the support composition will not impede normal eye tissue function of the host eye or the population of transplanted RPE cells. If the harvested RPE cells are to be cultured before transplantation, the composition providing support to the monolayer of RPE cells during transplantation may optionally be capable of serving as the attachment substrate for the RPE cells during culturing.

A variety of compositions may be used as the support for the population of RPE cells, depending upon the specific set of conditions to which the composition will be exposed after transplantation. In short, the composition is selected either because any portion remaining within the subretinal area for more than approximately one week after transplantation is compatible with normal eye tissue function upon exposure to bodily fluids within the sub-retinal area, or for its susceptibility to elimination upon exposure to prescribed conditions.

An additional factor to consider in determining the make-up of compositions for support of the monolayer of RPE cells is whether Bruch's membrane has been or will be removed from the host eye prior to transplantation of the monolayer of RPE cells. Bruch's membrane serves to anchor the RPE cells in a healthy eye. Removal of Bruch's membrane may occur in cases of AMD where a subretinal neovascular membrane has formed and Bruch's membrane is removed as a consequence of the removal of the neovascular membrane.

In cases where Bruch's membrane is removed, the support composition will comprise a layer of collagen less than 100 microns in thickness, and preferably between 1 and 10 microns in thickness. The basal surfaces of the RPE cells attach readily to the collagen layer, which serves to anchor the RPE cells to the choroid in place of the removed Bruch's membrane. The layer of collagen also serves to inhibit the occurrence or reoccurrence of subretinal neovascularization through and around the transplanted RPE. Such a collagen layer is retained indefinitely in the sub-retinal area. However, it is known that Bruch's membrane is essentially comprised of collagen, and such microthin layers of collagen are permeable enough to avoid impeding normal eye tissue functions such as the metabolic exchange between the choroid and the retina. However, collagen compositions of such a minimal thickness are not strong enough to prevent buckling or distortion of the monolayer of RPE cells during transplantation. Thus, such microthin collagen materials need to be used in combination with additional supporting materials which will be eliminated after transplantation, if they are to form part of the support for the transplanted RPE cells.

If transplantation is carried out with the native Bruch's membrane intact, the host's RPE cells covering the area to receive the transplant of RPE cells may be physically and/or chemically debrided from the Bruch's membrane, for example, by applying collagenase to the native Bruch's membrane to loosen the host's RPE cells in order to permit their removal. The transplanted RPE cells may then anchor themselves directly to the Bruch's membrane.

Either to supplement a layer of collagen, as discussed above, or in cases where inclusion of a collagen anchor is not required, a support composition may be selected which is dissipated, for example, by exposure to a sufficient amount of heat, selected enzymes, or bodily fluids. Gelatin is an example of a preferred support material which is flexible, lacks toxicity to neural tissue and has the ability to dissolve at body temperature. Another alternative is to use biodegradable polymers such as ethylene-vinyl acetate copolymer (Elvax 40W, DuPont Chemical Co., Delaware); poly (glycolic) acid, poly(L-lactide-co-glycolide)(70:30 ratio) or poly(L- or DL-lactic) acids (low mol. wt.) (Polysciences, Inc., Warrington, Pa., Data Sheet #365, 1990), which are flexible, non-toxic materials that slowly dissipate upon implantation and exposure to bodily fluids. See, e.g., Powell, E. M., *Brain Research*, 515 (1990) 309–311 and references cited in Polysciences, Inc. Data Sheet #365.

Advantageously, the gelatin or other support composition may additionally serve as a carrier for any of a number of trophic factors such as pharmacologic agents including immunosuppressants such as cyclosporin A, anti-inflammation agents such as dexamethasone, anti-angiogenic factors, anti-glial agents and anti-mitotic factors. Upon dissolution of the support composition, the factor or agent becomes available to impart the desired effect upon the surrounding tissue. The dosage can be determined by established experimental techniques.

With appropriate enzymatic digestion, using techniques disclosed by Pfeffer, B. A., Chapter 10, "Improved Methodology for Cell Culture of Human and Monkey Retinal Pigment Epithelium", *Progress in Retinal Research*, Vol. 10 (1991), at p.264, RPE cells are removed from the Bruch's membrane as intact sheets rather than as dissociated cells. Such a freshly harvested intact monolayer of RPE cells may be immediately apposed as an intact monolayer to a support, such as a thin collagen sheet, supplemented with an overlayer or substrate of gelatin, allowing several hours for adhesion prior to transplantation. This procedure may be useful for transplantation of RPE cells obtained in a biopsy, provided sufficient RPE tissue is obtained from the biopsy as an intact monolayer.

In most cases, however, it is preferable to culture the harvested RPE cells on an attachment substrate so that a monolayer of RPE cells may be prepared. Culturing the RPE cells before harvesting is also preferred both to allow for the production of larger populations of RPE cells from a small amount of harvested tissue and to allow for a period of observation to ensure that the RPE cells to be transplanted are healthy and functional.

For proper culturing, harvested RPE cells contained are apposed to a substrate to which they will attach and grow, and which is capable of being maintained in culture conditions appropriate for efficient growth of RPE cells. Apposition of RPE cells may be accomplished by pipetting a solution containing a population of RPE cells onto the substrate. Intact sheets of harvested RPE cells in a physiological solution may also be physically released via a wide-bore pipette onto the substrate and manipulated with a fine camel-hair brush if necessary. Since RPE cell cultures grow best at around 37° C., appropriate substrates are solids at this temperature. Attachment substrates which are suitable for growth of RPE cell cultures include plastic culture ware or glass culture chamber slides coated with collagen for cell attachmant.

Culturing harvested RPE cells can be accomplished by any suitable method for obtaining a confluent monolayer of RPE cells. Appropriate culturing techniques are described in Pfeffer, B. A., Chapter 10, "Improved Methodology for Cell Culture of Human and Monkey Retinal Pigment Epithelium", *Progress in Retinal Research*, Vol. 10 (1991); Ed. by Osborn, N. and Chader, J., or Mayerson, P. L., et al., "An Improved Method for Isolation and Culture of Rat Retinal Pigment Epithelial Cells", *Investigative Ophthalmology & Visual Science*, Nov., 1985, 26: 1599–1609.

FIG. 2 depicts a schematic of the preparation and transplantation of a preferred embodiment of the implant according to the invention. An implant laminate 1 is formed as depicted in FIGS. 2a and 2b. Gelatin 3 is preferred for use to provide monolayer support during transplantation because it is flexible, non-toxic to neural tissues, and because it dissolves away after exposure to body temperature (37° C.). However, since RPE grows too slowly at temperatures below 37° C., gelatin is not an appropriate substrate for use in culturing RPE cells. Thus, a monolayer of RPE cells 5 is first cultured on a suitable substrate for growth. RPE cells will grow on plastic culture ware A. However, to aid in removal of the monolayer of RPE cells 5 from the culture ware A, the culture ware A may be coated with a substrate 9 for the RPE cells, such as agarose or fibrin. See FIG. 2b. The substrate 9 is in turn coated with a thin (@2–4 microns) layer of collagen 7, to which the monolayer of RPE cells 5 readily attach, and which will serve as an anchor for the RPE cells in the post-transplantation period. If agarose is used as the substrate 9, the agarose is activated so that the collagen 7 will adhere to it by treating the surface of the agarose with an activator such as cyanogen bromide, as disclosed by Axen, R. et al., *Nature* (1967) 214: 1302–1304, or p-nitrophenyl chloroformate as disclosed by Wilchek, M. and Miron, T., *Biochemistry International* (1982) 4: 629–635.

Figure 2A:
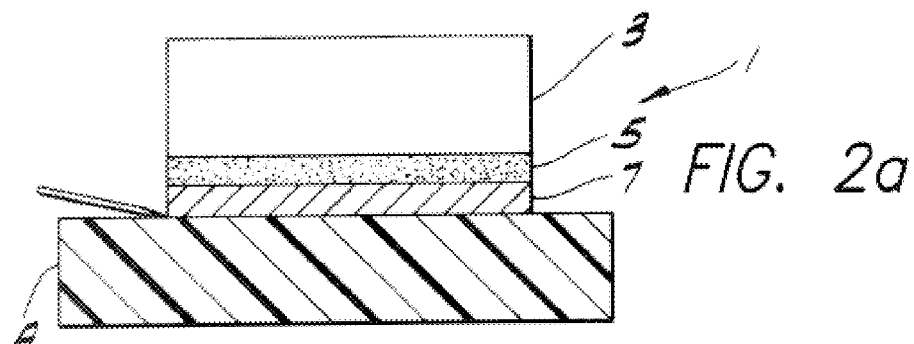
FIG. 2(a, b, c, d and e) is a schematic showing the preparation and transplantation of a preferred embodiment of an implant comprising a monolayer of RPE cells mounted to a support.

After a satisfactory culture of RPE cells has been grown, a 5 to 30% solution of molten gelatin is applied to the apical surface of the monolayer of RPE cells 5 in the culture. The culture ware containing the RPE cells and gelatin solution is then cooled so that the gelatin 3 is solidified into a sheet of preferably about 150–250 μm in thickness, attached to the apical surface of the RPE cells 5. The implant laminate 1 comprising a monolayer of RPE cells 5, attached to the collagen anchor 7 and an overlayer of gelatin 3, may then be physically removed from the culture ware A by slicing between the culture ware A surface and the collagen 7 with a razor C, as depicted in FIG. 2a.

Figure 2B:
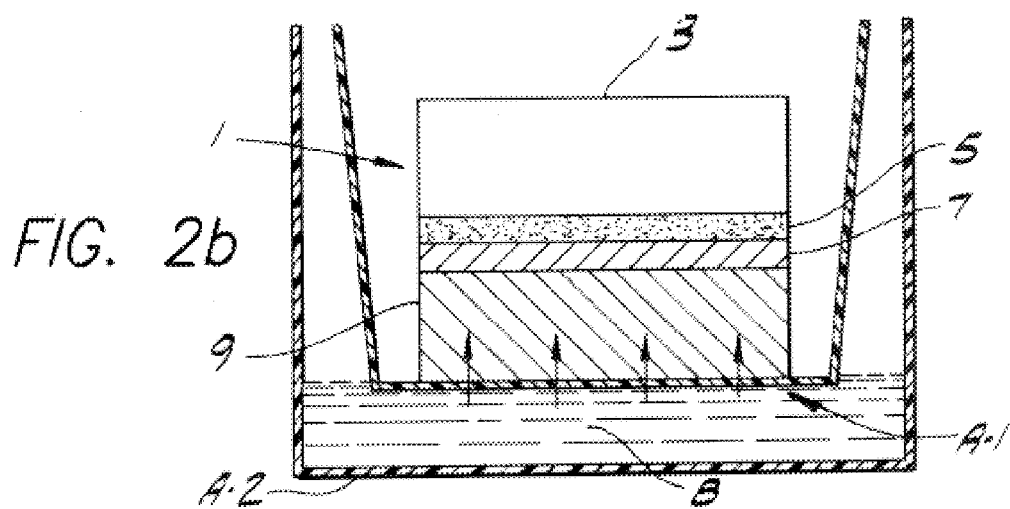

The implant laminate 1 may also be removed from the culture ware and substrate 9 enzymatically, as depicted in FIG. 2b. The underlying substrate 9 may be removed from the implant laminate 1 by application of an enzyme specific to the material comprising the substrate 9. If the substrate is agarose, agarase, an enzyme specific to agarose, may be used to dissipate the agarose. A concentration of 1 mg agarase/5 ml of culture medium will suffice to dissipate the agarose substrate. If the substrate consists of a fibrin coating, enzymes such as urokinase (2 activity units urokinase/ml of culture media) may be used to break apart the fibrin. To aid in dissipation of the substrate 9, the culture ware A may comprise a cell culture insert membrane, containing an inner membrane A-1 with a porous bottom, and an outer, solid membrane A-2. An example of such an insert membrane is the Falcon® Cyclopore™ membrane. The porous (e.g., pore size of 0.45 μm) inner membrane A-1 is coated with the substrate 9 during growth of the monolayer of RPE cells 5. These pores facilitate penetration of the solution B containing the enzyme into the substrate 9 so that it may be broken apart, and the implant laminate 1 removed from the culture ware A.

Figure 2C:
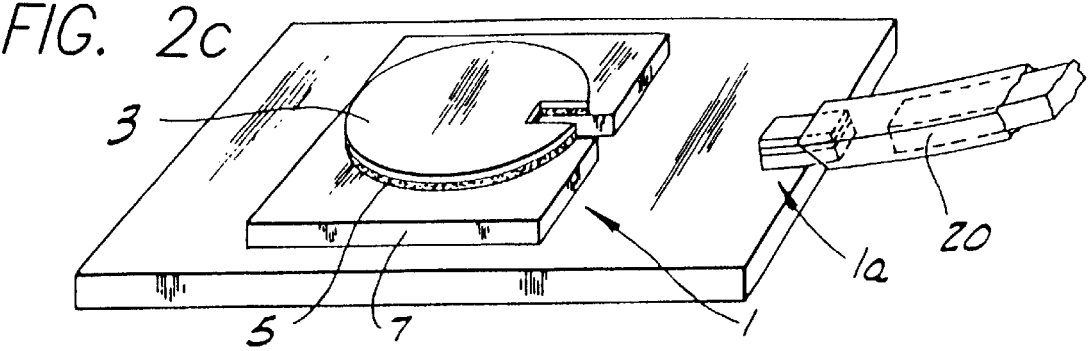
Figure 2D:
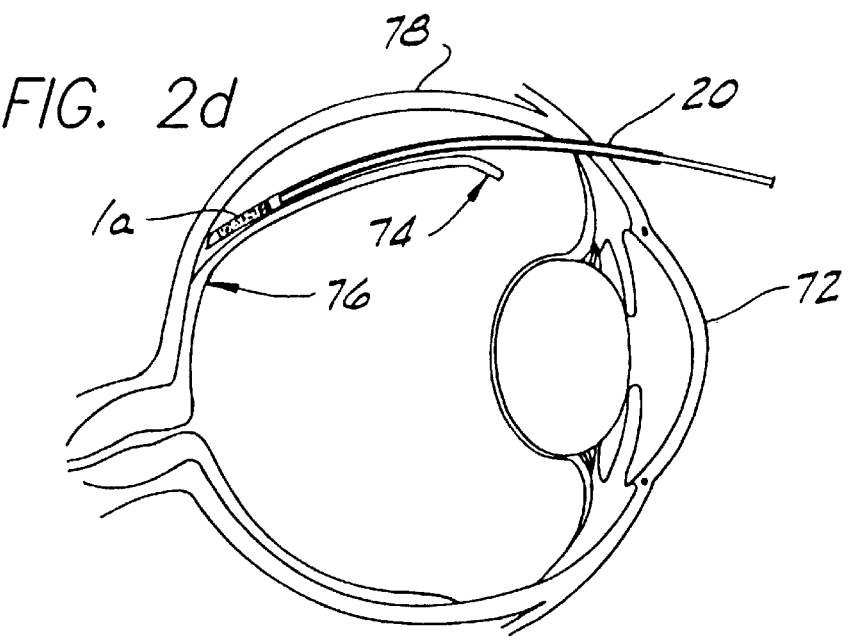
Figure 2E:
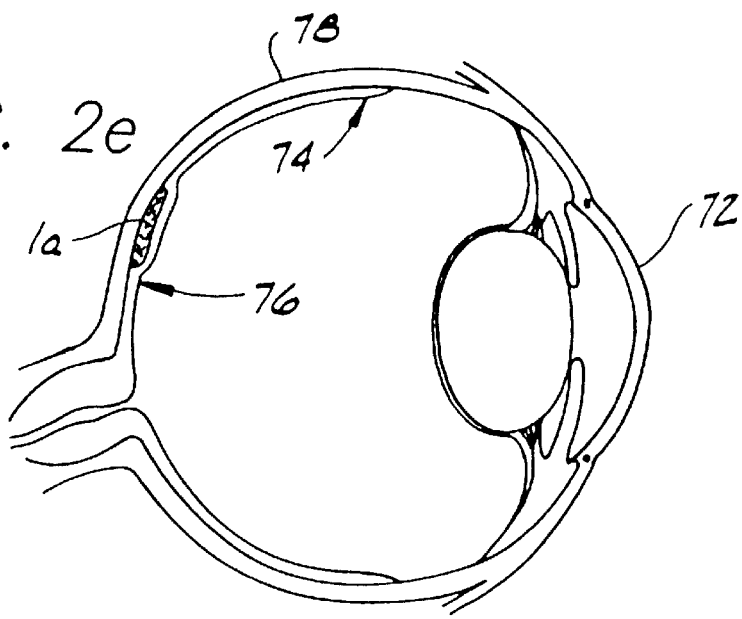
Figure 3:
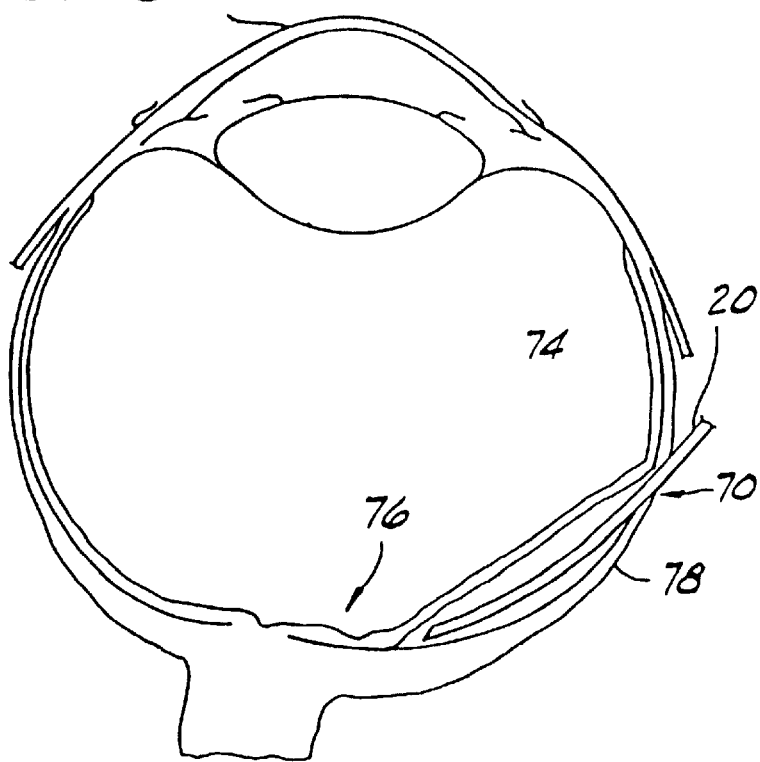
FIG. 3 is a horizontal section through an eye illustrating a transchoroidal and scleral surgical approach.

As depicted in FIG. 2c, the implant laminate 1 is cut to create an implant 1a sized so that it will fit into a surgical instrument 20 which contains a carrier channel for protection of the implant 1a during the transplantation procedure. The implant 1a is transplanted to the subretinal area at the posterior pole 76 of the host eye after detachment of the retina, as portrayed in FIG. 2d, using surgical techniques more fully disclosed below. The gelatin overlayer dissolves within hours after insertion of the implant 1a into the host eye. After transplantation, the retina reattaches, and the monolayer of RPE cells, anchored to the layer of collagen, is sandwiched between the choroid and the retina. See FIG. 2e.

Figure 4:
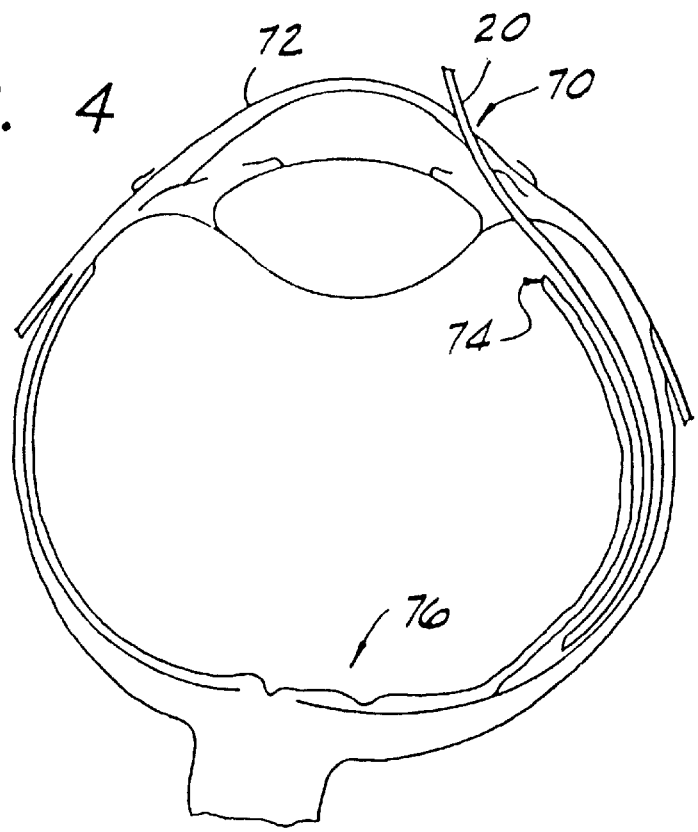
FIG. 4 is a horizontal section through an eye illustrating a transcorneal surgical approach.

To transplant the implant, the host eye is prepared so as to reduce bleeding and surgical trauma. A transcleral/transchoroidal surgical approach to the subretinal space is an example of a suitable approach and it will be understood that other surgical approaches, such as a transcorneal approach, may also be used. The preferred surgical approach in the human, FIG. 4, includes making a transverse incision 70 in a sclera and choroid 78 of sufficient size so as to allow insertion of a surgical instrument 20. The instrument 20 is advanced through the sclera and choroid 78 and to the ora serrata 74 as illustrated in FIG. 4. The instrument detaches the retina as it is advanced under the retina and into the sub-retinal space to the posterior pole 76 of the eye.

Preferably, an instrument comprising an elongate tube having a flat, wide cross-section may be used so that the implant may be drawn into the elongate tube for protection as it is transported through an appropriate sized incision in the sclera or choroid. The instrument is advanced to the ora serrata 74 of the host eye and if the instrument includes a lumen, the retina is detached by the gentle force of a perfusate such as a saline-like fluid, carboxymethylcellulose, or 1–2% hyluronic acid ejected from the lumen. Advantageously, the fluid may additionally contain anti-oxidants, anti-inflammation agents, anesthetics or agents that slow the metabolic demand of the host retina.

If the instrument does not include a lumen, the retina is detached by subretinal irrigation or by the walls of the surgical instrument as it is advanced under the retina and into the subretinal space to the posterior pole 76 of the eye. The implant is then transplanted by retracting the tube containing the implant from the eye while simultaneously gently ejecting the implant from the tube. The instrument is then carefully withdrawn out of the eye. Retinal reattachment occurs rapidly and the monolayer of RPE cells is held in place in a sandwich-like arrangement between the retina and the choroid. The incision may require suturing.

FIG. 4 depicts a transcorneal surgical approach as an alternative to the transscleral and choroidal approaches described above. Except for the point of entry, the surgical technique is essentially the same as outlined for the transscleral or choroidal approaches. A transverse incision 70 is made in a cornea 72 and the instrument 20 containing the implant is advanced under the iris, through the cornea 72 and to the ora serrata 74 as illustrated in FIG. 4. The iris should be dilated for example, with topical atropine. The edges of the corneal incision are abutted and sutured if necessary to allow healing. The transcorneal approach is preferred for rodents because it has been found to reduce bleeding and surgical trauma. Nevertheless, a transscleral or choroidal approach is preferred for humans to avoid scarring of the cornea which may interfere with visual acuity.

A further surgical approach is to diathermize in the pars planna region to eliminate bleeding. The sclera is then incised and the choroidal and any native epithelial tissue is diathermized. The surgical tool is then inserted through the incision, the retina is intercepted at the ora serrata and the implant is deposited in the subretinal area otherwise as outlined elsewhere herein.

In yet a further surgical approach, entry is gained through the pars planna area as outlined above and an incision is made in the retina adjacent to the retinal macula. The surgical tool is then inserted through the retinotomy and into the macular area.

As discussed previously in connection with the make up of the support compositions used in accordance with the invention, after transplantation, the implant is exposed to a predetermined set of conditions, such as exposure to heat or bodily fluids. Upon the appropriate amount of exposure, the support composition is dissipated or will not otherwise impede normal eye tissue function of the host eye and the transplanted population of RPE cells.

The following examples illustrates the invention.

EXAMPLE 1

Experimental Animal and Materials

RPE cells were taken from the sub-retinal area of donated human eyes (obtained from the Missouri Lions and St. Louis Eye Banks) following corneal removal. Hosts were adult albino rats immune-suppressed with cyclosporin A 10 mg/kg/day IP injection).

Harvesting of RPE Cells

Immediately after corneal removal, the eye was pinned by the optic nerve stump into an eye cage and placed into an eye jar. The jar was flooded to capacity with cold Dulbecco's modified essential medium (DMEM), supplemented with 5% fetal bovine serum. The eye was processed in a sterile environment. After loose connective tissue and muscle were carefully trimmed from the eye, it was placed upright on a sterile plate and the anterior segment with the adherent vitreous was lifted out of the eye cup. Four slits were cut radially toward the optic disc with the eye lying flat in a petri dish. The neural retina was then separated at the optic disc and removed. The shell was then washed with Hanks' balanced salt solution, Ca++ and Mg++ free, and treated with 0.25% trypsin for 30 min. at 37° C. The trypsin solution was aspirated from the shell and DMEM (GIBCO) was added. The cells were released from Bruch's membrane by gently brushing the surface of the RPE cells with the polished tip of a pasteur pipette and pipetting the culture medium in the shell.

Culturing of RPE Cells

Glass culture chamber slides were prepared by coating them with liquid collagen obtained from Sigma Chemical Co., St. Louis. The collagen was allowed to solidify to about 150 microns in thickness. $3 \times 10^5$ RPE cells were plated onto the prepared slides using a pasteur pipette. The RPE cells were then incubated in DMEM+F12 (1:1. GIBCO) supplemented with 20% fetal bovine serum (Sigma Chemical Co., St. Louis). The culture medium was changed every 3–4 days until a confluent monolayer of RPE cells had been cultivated. Implants comprising monolayers of RPE cells laminated to collagen were removed from the culture chamber slides and sheets of approximately 2 mm×4 mm were cut out for transplantation.

Surgical Procedure

A transverse incision was made in the cornea sufficient to allow insertion of a surgical instrument that is 2.5 mm wide with a lumen 0.5 mm high. The instrument was advanced under the iris (dilated with topical atropine) to the ora serrata, detaching the retina. The carrier was then advanced under the retina into the subretinal space to the posterior pole of the eye. The instrument allowed an implant comprising a monolayer of RPE cells apposed to a 150 $\mu$m collagen substrate (up to 2.5×4 mm) to be guided into the retinal space by advancement of the plunger with simultaneous retraction of the surgical instrument. The instrument was then removed. Following removal of the instrument, the edges of the corneal incision were abutted to allow rapid, sutureless healing. The eye was patched during recovery and a prophylactic dose of penicillin was administered. Upon removal of the patch, a veterinary ophthalmic antibiotic ointment was applied.

Transplant recipients were maintained on a 12 hr/12 hr light/dark cycle with an average light intensity of 50 lux. Following appropriate survival times, the animal was overdosed with pentobarbital.

Figure 5:
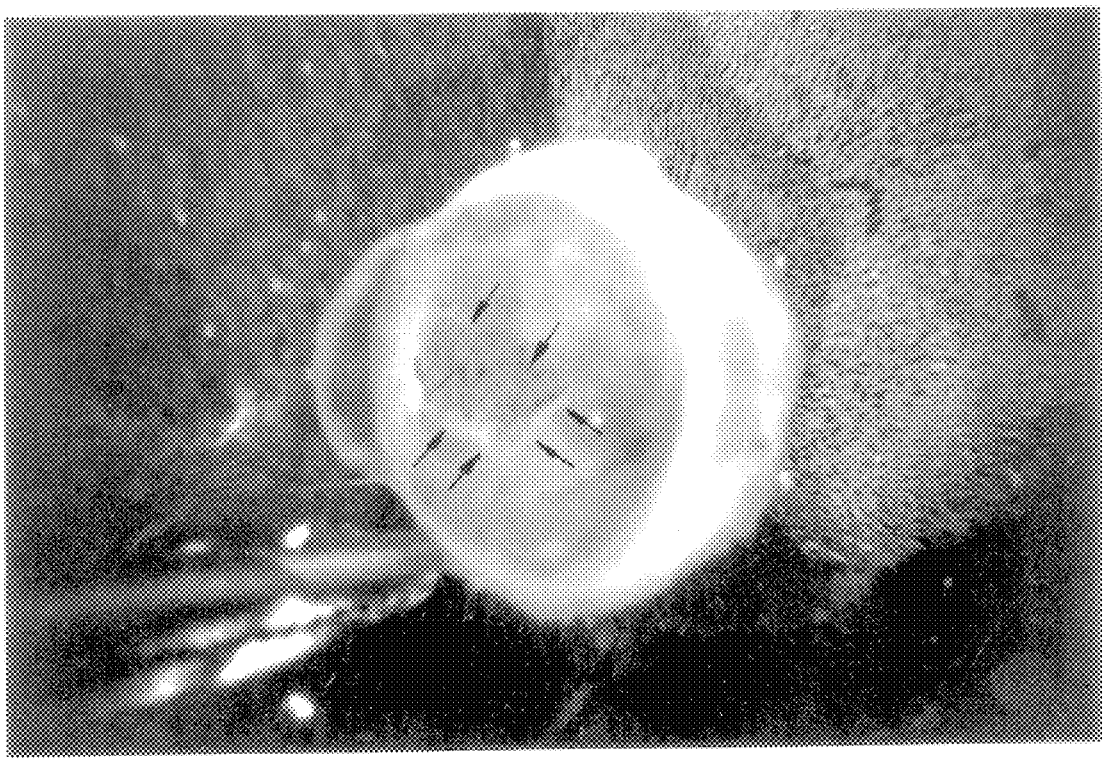
FIG. 5 is a photograph showing a view of the transplanted implant of an intact monolayer of mature human RPE cells positioned under the retina of a rodent whose cornea, pupil and lens have been removed, 2 weeks post-transplantation, as set forth in Example 1.

FIG. 5 shows a view of the transplanted monolayer of RPE cells positioned under the retina, with the cornea, pupil and lens removed, two weeks post-transplantation. The arrows designate the edges of the implant.

Histologic Preparation

For histologic evaluation, rat eyes with RPE cell implants were immersion-fixed in Bouin's solution for 5 hrs., then dehydrated in a graded ethanol series. The eyes were trimmed with a razor blade to include the transplanted area for implanted retinas, then processed through xylene and embedded in paraffin. Sections were cut at 8 $\mu$m and stained with hematoxylin and eosin.

Results

By using the transcorneal approach, it was found that the positioning of the monolayer of RPE cells between the host's retina and the adjacent choroidal tissue layer of the eye could be accomplished while minimizing the vascular damage and subsequent bleeding into the eye. In addition, it was found that this approach does not appear to disrupt the integrity of the retina, which reattaches to the back of the eye with the transplanted RPE cells interposed between the retina and the choroid. Using this insertion method, it was possible to position the RPE cells beneath the posterior pole of the retina (FIG. 6).

To determine the viability of the transplanted RPE cells, paraffin sections (8 $\mu$m) were made from the eye receiving the RPE cell transplant at 2 weeks, 4 weeks, and 3 months after transplantation. It was found that the monolayer of RPE cells survived transplantation at all times tested (10 out of 12 transplants).

Figure 6:
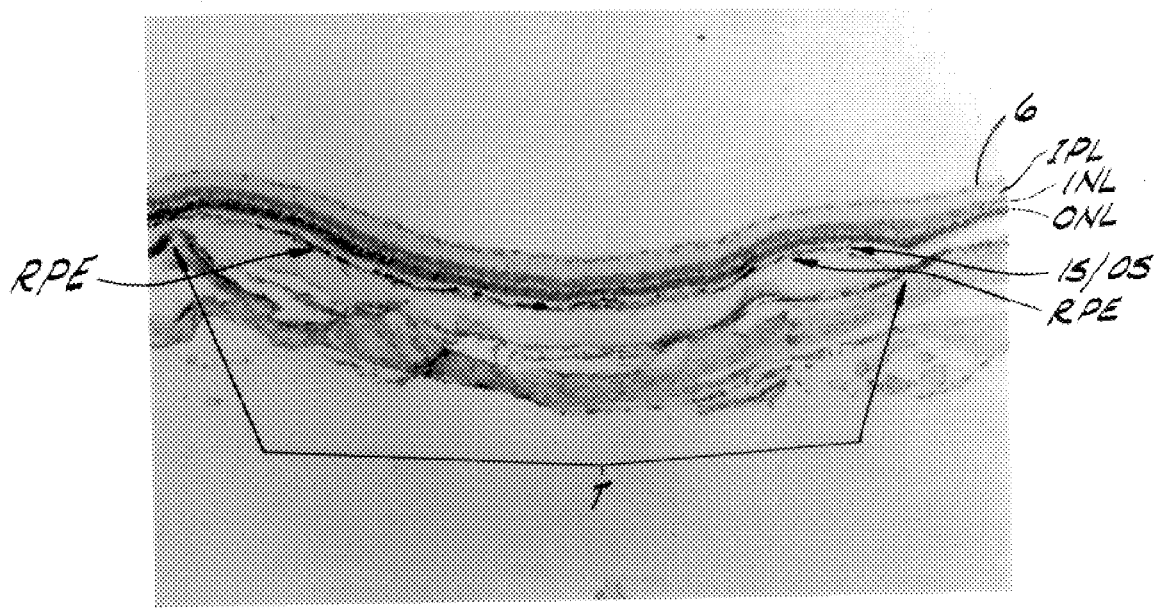
FIG. 6 is a photograph (40×) of a section of a rat retina and sub-retinal area showing an implant of an intact monolayer of a population of mature human RPE cells 14 days after transplantation, as set forth in Example 1.

With immune-suppression, successful transplants were seen at all survival times so far examined (2 weeks to 3 months), showing apparent physical integration with the host eye and maintaining morphological features of the RPE as illustrated in FIG. 6 which shows a transplant of a monolayer of human RPE cells from adult donor to adult rat host. (T, transplant). 40×.

Figure 7:
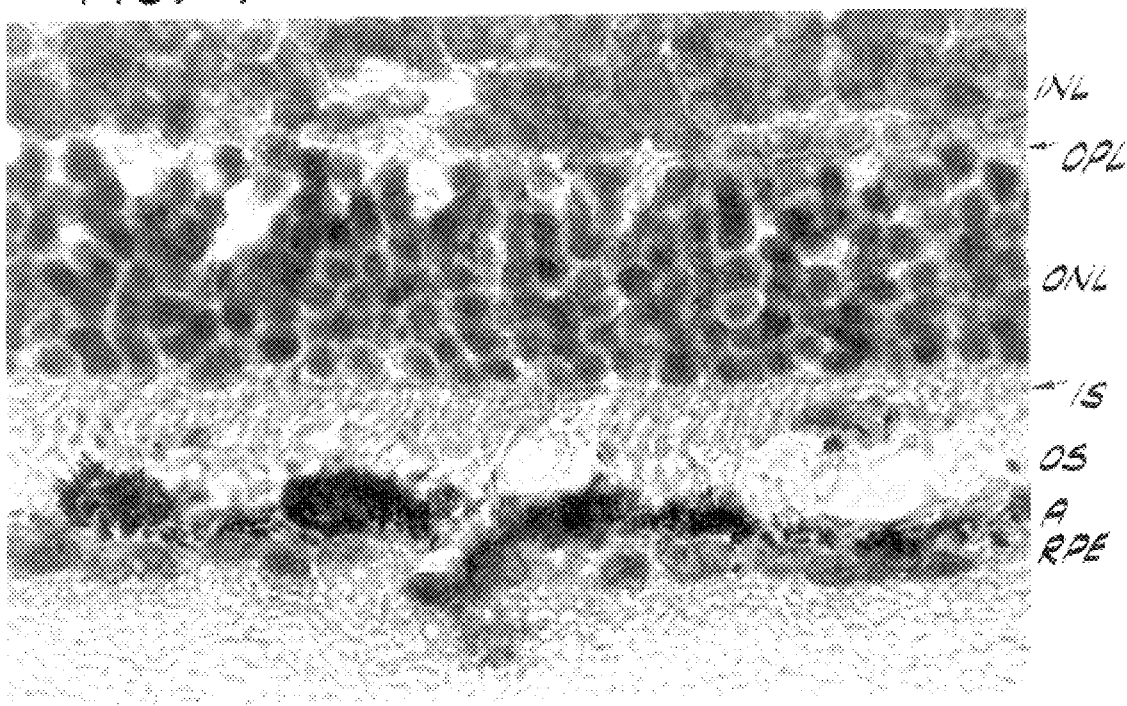
FIG. 7 is a higher magnification photograph (400×) of a section of a rat retina and sub-retinal area showing an implant of an intact monolayer of a population of mature human RPE cells 14 days after transplantation, as set forth in Example 1.

Paraffin sections made at 2 weeks post-transplantation are shown in FIGS. 6 and 7. FIG. 6 is a low-power photomicrograph showing the location of the RPE monolayer transplant (T) between arrowheads at the posterior pole of th host eye. Note the maintenance of normal retinal configuration as well as the normal appearance of the RPE cells, maintained in substantially a monolayer between the choroid and the outer segments of the photoreceptor cells. FIG. 7 is a higher-power photomicrograph showing in detail the interface between the transplant and the adjacent retina. As shown in FIG. 7, the photoreceptor outer segments are shown to be in normal apposition to the apical microvillar processes (A) of transplanted RPE cells.

The functional capabilities of the transplanted RPE cells and reconstructed retina were ascertained by their maintenance of photoreceptor bodies, and the presence of inner and outer segments with proper orientation to the apical processes of transplanted RPE cells. The success of these procedures for transplanting monolayers of RPE cells are reflected in FIGS. 6 and 7.

EXAMPLE 2

As a comparison, mature human RPE cells were transplanted in dissociated form using the bolus injection method as set forth by Li and Turner in *Exp. Eye Res.*, 47:911 (1988). RPE cells from the same donor tissue used for the transplants conducted as set forth in Example 1 were harvested and cultured as set forth in Example 1. After culturing, the RPE cells were trypsonized to form dissociated RPE cells for transplantation by bolus injection according to the method of Li and Turner. Hosts were adult albino rats inmune-suppressed with cyclosporin A 10 mg/kg/day IP injection) as set forth in Example 1.

Transplant recipients were maintained on a 12 hr/12 hr light/dark cycle with an average light intensity of 50 lux. Following appropriate survival times, the animal was overdosed with pentobarbital. Paraffin sections of the eye receiving the RPE cell implant were then cut (8 $\mu$m).

Figure 8:
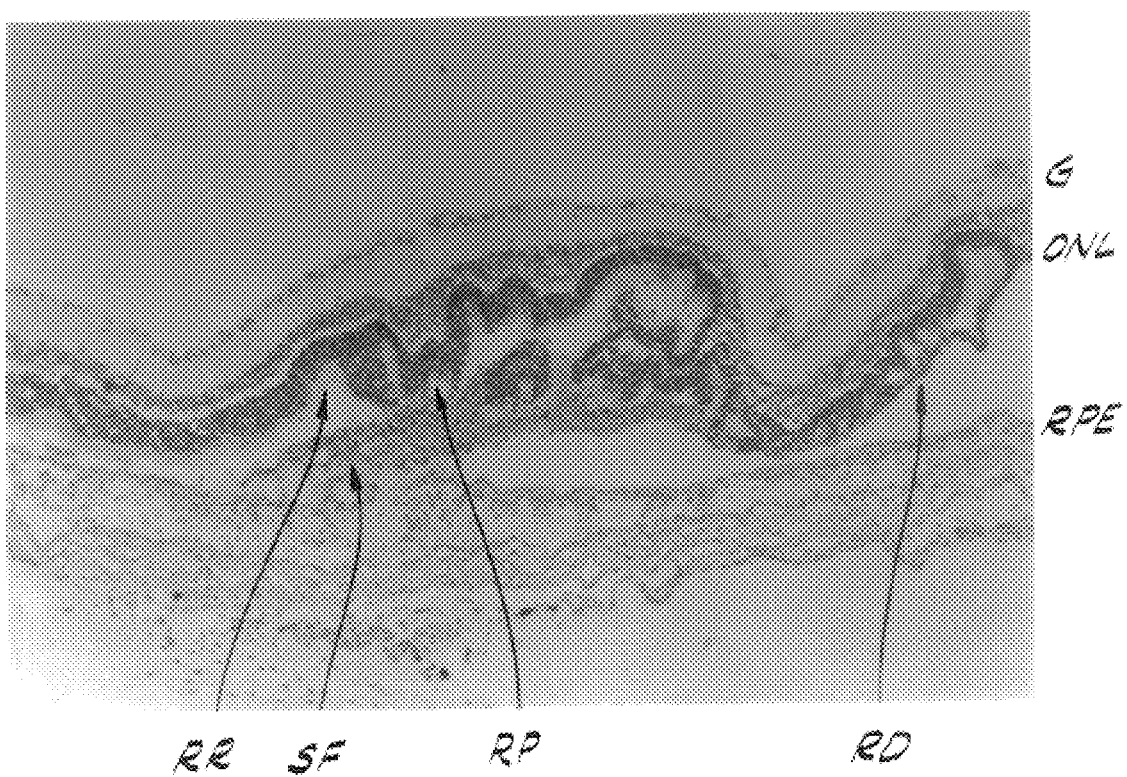
FIG. 8 is a photograph (100×) of a section of a rat retina and sub-retinal area 14 days after transplantation of dissociated mature human RPE cells, as set forth in Example 2.
Figure 9:
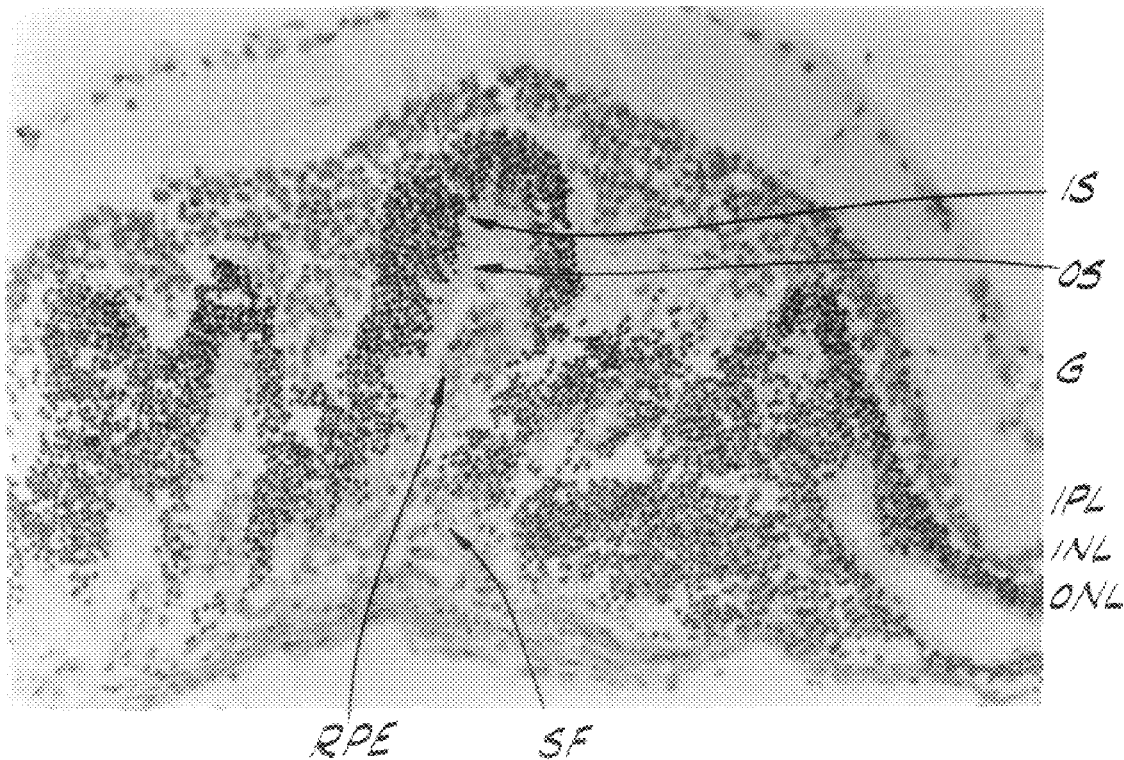
FIG. 9 is a higher magnification photograph (300×) of a section of a rat retina and sub-retinal area 14 days after transplantation of dissociated mature human RPE cells, as set forth in Example 2.

Paraffin sections made at 2 weeks post-transplantation are shown in FIGS. 8 and 9. FIG. 8 is a low-power photomicrograph showing the location of the injection of dissociated RPE cells at the posterior pole of the host eye. Note the pathological configurations, including retinal detachment (RD), retinal pucker (RP), subretinal fibrosis (SF) and retinal rosette (RR) formation. FIG. 9 is a higher-power photomicrograph showing in detail the pathological invasion of RPE cells into the adjacent retina, subretinal fibrosis and retinal pucker.

From the foregoing description those skilled in the art will appreciate that all aspects of the present invention are realized. The present invention provides an improved surgical implant that is adapted to provide cell organization during transplantation of the RPE cells. With the implant of this invention cell organization is maintained during and after RPE transplantation.

In view of the above, it will be seen that the several objects of the invention are achieved and other advantages attained.

As various changes could be made in the above compositions and methods without departing from the scope of the invention, it is intended that all matter contained in the above description or shown in the accompanying drawings shall be interpreted as illustrative and not in a limiting sense.

What is claimed:

1. A method for the preparation of a retinal pigment epithelial cell graft for transplantation to the subretinal space of a host's eye comprising the steps of:
   a) providing donor tissue comprising retinal pigment epithelial cells;
   b) harvesting retinal pigment epithelial cells from the donor tissue;
   c) culturing the harvested retinal pigment epithelial cells on a culture substrate to form a monolayer said substrate being transplantable to the subretinal space and upon transplantation will not impede normal eye tissue function; and
   d) apposing the cultured retinal pigment epithelial cell monolayer to a non-toxic flexible support that, upon transplantation to the subretinal space, will not impede the host's normal eye tissue function nor will it impede the normal eye tissue function of the transplanted retinal epithelial cells.

2. A method as set forth in claim 1 wherein the donor tissue is autologous to the host.

3. A method as set forth in claim 1 wherein the support comprises a layer of collagen between about 1 micron and about 100 microns in thickness.

4. The method of claim 1 wherein the harvested retinal pigment epithelial cells have apical and basal surfaces, the culture substrate comprises collagen and the support comprises gelatin, and the basal surfaces of the harvested retinal pigment epithelial cells are apposed to the collagen and apical surfaces of the harvested retinal pigment epithelial cells are apposed to the gelatin, wherein said retinal pigment epithelial cells are between said collagen and said gelatin.

5. A method as set forth in claim 1 wherein the harvested retinal pigment epithelial cells have an apical surface and apposition of the retinal pigment epithelial cells to the support further comprises contacting the apical surface of the retinal pigment epithelial cells to the support.

6. The method of claim 1 wherein said support comprises a material which degrades upon transplantation.

7. A graft capable of transplantation to the subretinal space formed by the method of claim 1.

8. A graft capable of transplantation to the subretinal space formed by the method of claim 3.

9. A graft capable of transplantation to the subretinal space formed by the method of claim 4.

* * * * *